United States Patent [19]

Baecklund et al.

[11] Patent Number: 5,050,201
[45] Date of Patent: Sep. 17, 1991

[54] APPARATUS INCORPORATING A MEASURING HEAD

[75] Inventors: Johannes Baecklund; Lars Börjesson, both of Oskarshamn, Sweden

[73] Assignee: Refina Instrument AB, Sweden

[21] Appl. No.: 523,874

[22] Filed: May 16, 1990

[30] Foreign Application Priority Data

May 17, 1989 [SE] Sweden .............................. 8901764-4

[51] Int. Cl.⁵ ........................ G21K 1/00; H01J 35/16; H05G 1/00
[52] U.S. Cl. .................................... 378/161; 378/203; 378/204; 378/210; 242/67.3 R
[58] Field of Search ............... 378/210, 171, 175, 161, 378/203, 204; 242/67.3 R

[56] References Cited

U.S. PATENT DOCUMENTS

| | | | |
|---|---|---|---|
| 3,510,648 | 5/1970 | Leger, Jr. | 250/301 |
| 3,848,133 | 11/1974 | Blanc et al. | 378/171 |
| 4,104,528 | 8/1978 | Strax | 378/171 |

Primary Examiner—Edward P. Westin
Assistant Examiner—Don Wong
Attorney, Agent, or Firm—Larson & Taylor

[57] ABSTRACT

An apparatus provided with a measuring head for determining with the aid of X-ray fluorescence or X-ray absorption measuring techniques the surface weight of a measuring subject comprising coatings or surface-deposits or the concentration of basic substances in the subject to be measured, comprising liquid, slurries, powder or solid samples. The apparatus includes means for moving the measuring head (1) over the subject (5) to be measured and also over a reference sample (4), such as a sample or an empty sample-container, or vice versa. The measuring aperture provided in the measuring head (1) is covered with a protective film (7) for the purpose of preventing the ingress of particles from the subject (5) into the aperture. Means (3) are also provided for checking the dirt-coating on the protective film (7) regularly and for sending an order to a film-carrying device (8, 10, 11) to advance film when the dirt-coating is found unacceptable.

4 Claims, 3 Drawing Sheets

APPARATUS INCORPORATING A MEASURING HEAD

The present invention relates to an apparatus which incorporates a measuring head and which is intended for determining by X-ray fluorescence or X-ray absorption measuring techniques the surface weight of such measuring subjects as coatings and surface deposits, or the concentration of elements in such measuring subjects as liquids, slurries, powders or solid samples, and which apparatus also incorporate means for moving the measuring head over the subject to be measured and over a reference sample, or vice versa.

The object of the present invention is to provide an apparatus of the aforesaid kind by means of which dirt-deposits collecting on a protective film can be monitored regularly and clean film can be advanced to and positioned above the measuring aperture.

The novel and characteristic features of the invention reside in the provision of a protective film over the measuring aperture of the measuring head, such as to prevent the ingress of particles into said aperture from the subject being measured, and also in the provision of means operative to check the protective film regularly for the presence of dirt coatings on said film, e.g. by effecting measurements on a reference sample, and also means for ordering and causing a film-holding device to advance clean film to a position above said aperture when the detected dirt-coating is unacceptably heavy or thick.

According to one particular embodiment of the invention, the film is carried by a spool device which has a winding-on or drive side, on which a motor is mounted, and a winding-off side which is provided with a rotation-indicator operative to confirm that film has actually been advanced in response to a film-advance order, and the measuring head is provided with electronic means operative to receive information to the effect that the spool on the winding-off side of the spool device is empty, or alternatively when the spool on the winding-on side is full, depending on which of these alternatives is fulfilled first.

The invention will now be described in more detail with reference to an exemplifying embodiment of an inventive apparatus provided with a measuring head and an associated spool device shown schematically in the accompanying drawings, in which FIG. 1 is a perspective view of the inventive apparatus;

Figure 1:
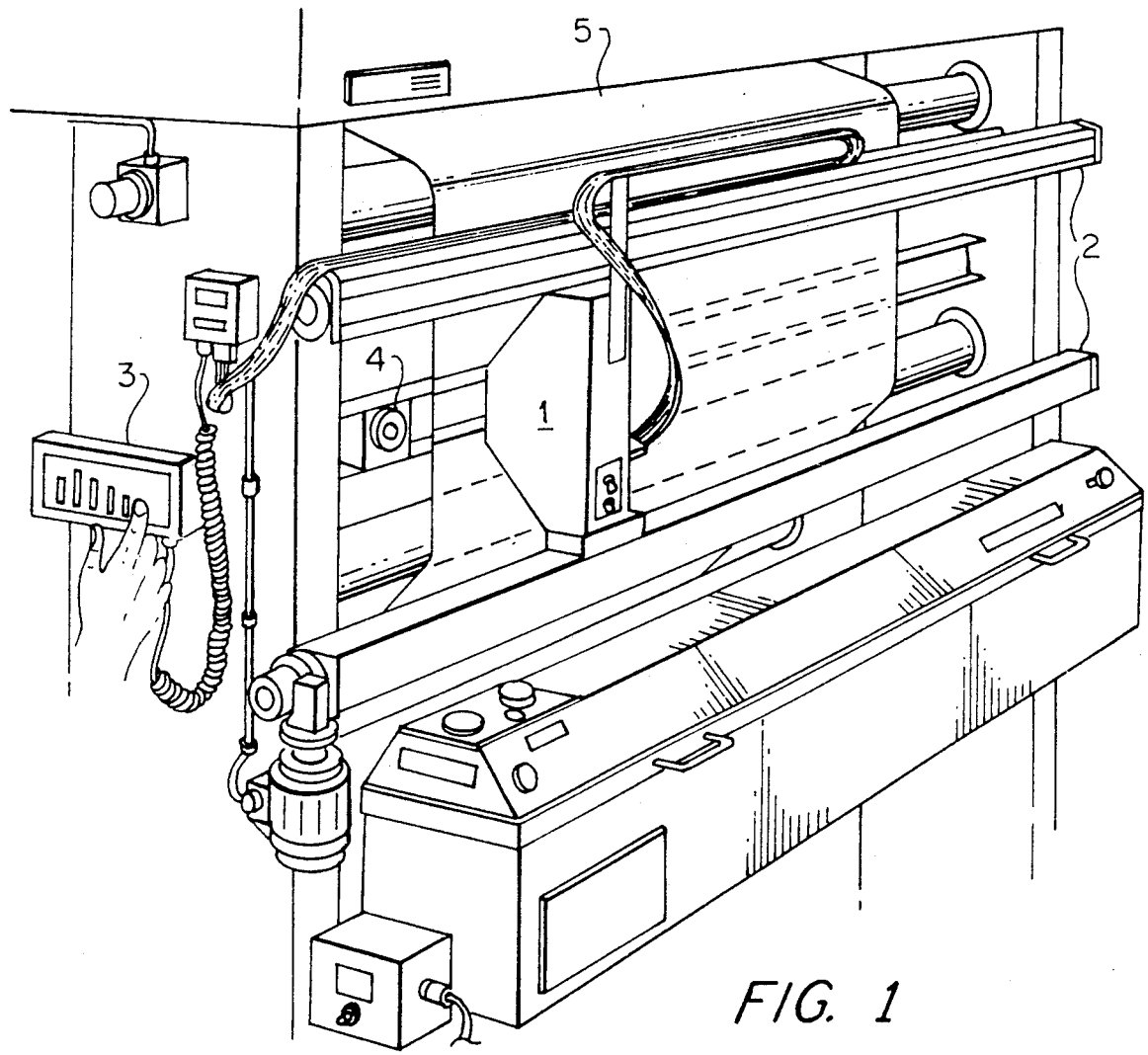

FIG. 1 illustrates an apparatus constructed in accordance with the invention and comprising a measuring head 1, a traverse (i.e. guide and support rails) 2 which carries the measuring head 1, electronic means 3, a reference sample 4, and a measuring subject 5 whose thickness is to be determined.

Figure 2:
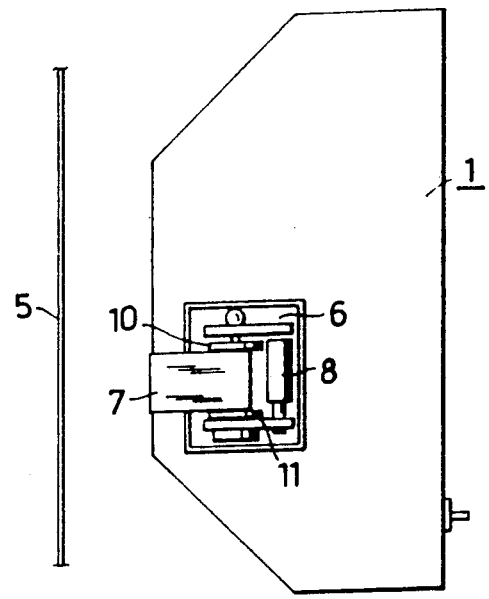
FIG. 2 is a side view of the measuring head seen from the winding-on side of the spool device.

FIG. 2 illustrates the measuring head 1 with the winding-on side or drive-side 6 of the spool device and a protective film 7. Also illustrated in FIG. 2 is a drive motor 8 for winding film 7 onto an empty spool disposed between spool wheels 10 and 11.

Figure 3:
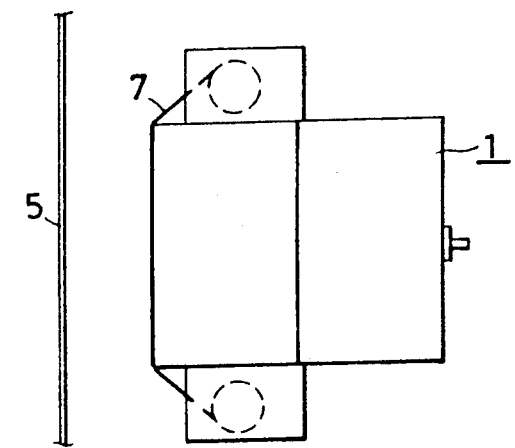
FIG. 3 is a front view of the measuring head illustrated in FIG. 2.
Figure 4:
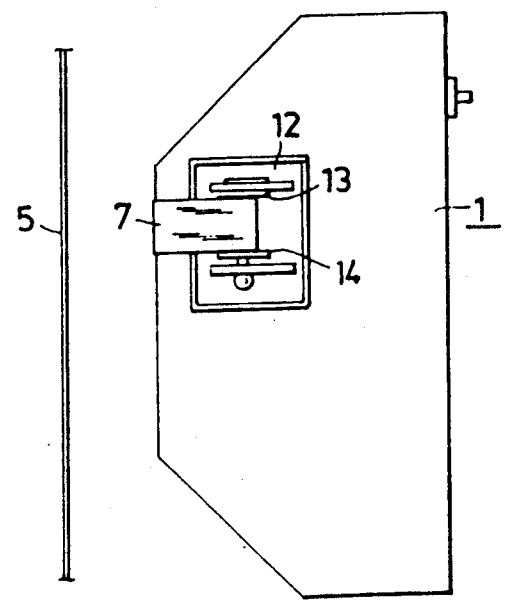
FIG. 4 is a side view of the measuring head seen from the winding-off side of the spool device.

FIG. 4 illustrates the measuring head 1 with the winding-off side 12 of said spool device, the film 7 being disposed on a spool which is clamped between spool wheels 13 and 14 The measuring object 5 whose thickness is to be checked/or controlled is also illustrated in FIGS. 2, 3 and 4.

Figure 5:
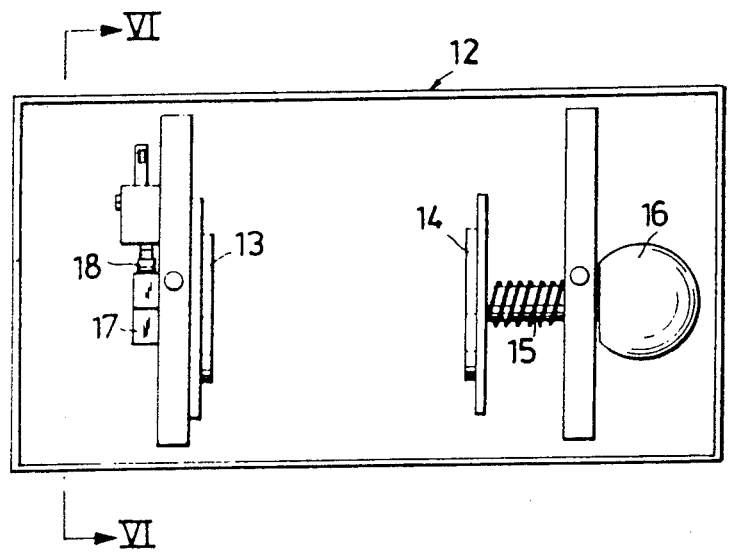
FIG. 5 is a side view of the winding-off side of the spool device, shown in larger scale than in FIG. 4.
Figure 6:
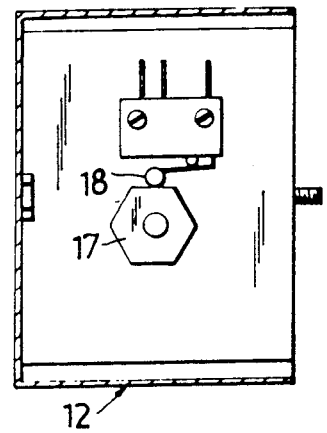
FIG. 6 is an end view of the winding-off side of the spool device illustrated in FIG. 5.

In the embodiment of the winding-off part 12 of the spool device illustrated in FIG. 5, the film-carrying spool is clamped between spool wheels 13 and 14 with the aid of a spool lock means comprising a pressure spring 15 and a pull-knob 16. The winding-off part 12 is also provided with an hexagonal wheel 17 and a microswitch 18 which is electrically connected to the electronic means 3 of the measuring head and which is operative to indicate spool rotation. The spool wheel 13 is a braked spool wheel.

Figure 7:
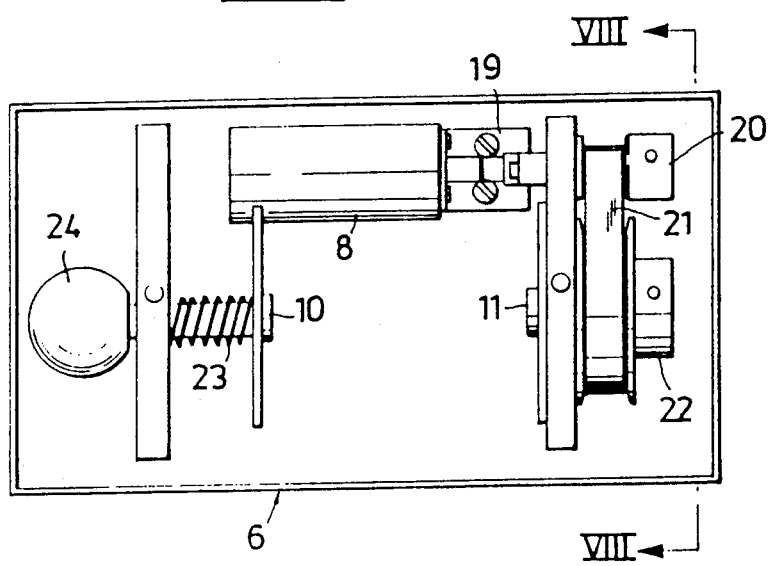
FIG. 7 is a side view of the winding-on side of the spool device, shown in larger scale than in FIG. 2.
Figure 8:
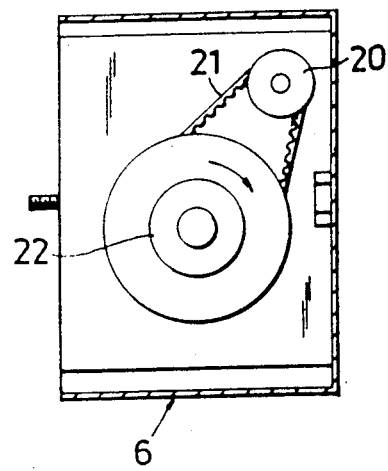
FIG. 8 is an end view of the winding-on side of the spool device illustrated in FIG. 7.

The winding-on part 6 of the spool device illustrated in FIGS. 7 and 8 is provided with a 12 volt d.c. motor 8, which is coupled, via an Oldham coupling 19, to a gear wheel 20 which drives a gear wheel 22, via a toothed belt 21, and therewith the drive wheel 11 on which the empty spool is fixedly mounted between said wheel and the spool wheel 10, said spool wheel 10 being spring biased by means of a pressure spring 23 provided with a pull-knob 24. The spool device operates in the following manner:

The spool provided with fresh and clean plastic film is positioned between the wheels 13, 14 on the winding-off part of the device, by pulling the pull-knob 16 to a quick-locking position. The spool may have a width of 50 mm, an inner diameter of 25 mm and an outer diameter of 40 mm. Film is then drawn from the spool, beyond the beam aperture of the measuring head 1, and up onto the empty spool on the winding-on side 6 of the device, where said film-spool is clamped between the wheels 10, 11, by pulling out the pull-knob 24 to a quick-locking position. The spool device is then ready for operation. The hexagonal indicator wheel 17 is forced to rotate when the motor 8 on the winding-on side advances the film, and the indicator wheel, in turn, activates the microswitch 18 electrically connected to the electronic means of the measuring head. If the electronic means fails to receive signals from the microswitch 18, despite the fact that the motor is in operation, this means that the film is exhausted. Also provided on the winding-on side of the spool device is a mechanical switch (not shown) which is activated when the diameter of the film wound onto respective spools exceeds the diameter of respective wheels 10, 11, which can occur when the coating of dirt on the film is abnormally thick. Considering the overall operation of the apparatus of FIGS. 1-8, as set forth above, the electronic means 3 can be used to check the protective film on a regular basis for the presence of a dirt coating on the film by, in the example illustrated, effecting measurements on the reference sample 4 using the measuring head 1, i.e., with the measuring head positioned "over" i.e., in front of or in registration with, sample 4. Such a measurement can be compared with an initial, calibrating measurement result used as a standard or a reference so as to determine whether the amount of dirt buildup on the film 7 exceeds a predetermined limit. As was also stated previously, a command signal can then be sent to the drive-side 6 of the spool device for the protective film 7 to provide for advancing of clean film to a position above the beam measuring aperture of the measuring head 1 when the detected dirt coating is unacceptable heavy or thick, i.e., where the predetermined limit is exceeded.

What is claimed is:

1. Apparatus including a measuring head and intended for determining with the aid of X-ray fluorescence or X-ray absorption measuring techniques the surface weight of a test subject comprising coatings or surface deposits, or for determining the concentration of basic substances in a test subject in the form of liquids, slurries, powder or solid samples, said apparatus including means for providing relative movement between the measuring head and the test subject so as to enable the measuring head to measure the test sample and between the measuring head and a reference sample so as to enable the measuring head to measure the reference sample the improvement wherein the measuring head includes a measuring aperture covered with a protective film for preventing the ingress of particles from the test subject into said aperture, and wherein said apparatus further comprises a film movement control device, in which said film is arranged, for controlling advancing of said film and means for enabling dirt coatings on the protective film to be checked regularly and for sending to said film movement control an instruction to advance film when the dirt coating is found to be unacceptable.

2. Apparatus according to claim 1, wherein the means for regularly checking the dirt coating includes electronic means for receiving signals from said measuring head when said measuring head measures the reference sample.

3. Apparatus according to claim 1, wherein the film movement control device comprises a spool device comprising a winding-on spool and a winding-off spool disposed on respective sides of the measuring aperture of the measuring head, a motor for driving the winding-on spool and a rotation indicator connected to the winding-off spool for indicating advancing of the protective film.

4. Apparatus according to claim 1 wherein said apparatus comprises guide and support rails between which said measuring head is mounted and along which said measuring head moves.

* * * * *